US010010429B2

United States Patent
Dmuschewsky

(10) Patent No.: US 10,010,429 B2
(45) Date of Patent: Jul. 3, 2018

(54) INTERVERTEBRAL CAGE WHICH IS EXPANDABLE IN STEPS AND IMPLANTATION INSTRUMENT THEREFOR

(71) Applicant: FACET-LINK INC., Rockaway, NJ (US)

(72) Inventor: Klaus Dmuschewsky, Hamburg (DE)

(73) Assignee: FACET-LINK INC., Rockaway, NJ (US)

( * ) Notice: Subject to any disclaimer, the term of this patent is extended or adjusted under 35 U.S.C. 154(b) by 0 days.

(21) Appl. No.: 15/318,629

(22) PCT Filed: Jun. 13, 2014

(86) PCT No.: PCT/EP2014/062461
§ 371 (c)(1),
(2) Date: Dec. 13, 2016

(87) PCT Pub. No.: WO2015/188887
PCT Pub. Date: Dec. 17, 2015

(65) Prior Publication Data
US 2017/0112632 A1    Apr. 27, 2017

(51) Int. Cl.
*A61F 2/44* (2006.01)
*A61B 17/88* (2006.01)
(Continued)

(52) U.S. Cl.
CPC ............ *A61F 2/447* (2013.01); *A61F 2/4611* (2013.01); *A61F 2/4637* (2013.01);
(Continued)

(58) Field of Classification Search
CPC ...... A61F 2/447; A61F 2/4611; A61F 2/4637; A61F 2002/30377; A61F 2002/30477;
(Continued)

(56) References Cited

U.S. PATENT DOCUMENTS 5,723,013 A    3/1998  Jeanson et al.
5,865,848 A    2/1999  Baker
(Continued)

FOREIGN PATENT DOCUMENTS

DE    40 12 622    7/1991
FR    2 730 158    8/1996
(Continued)

OTHER PUBLICATIONS

International Search Report dated Feb. 23, 2015, directed towards International Application No. PCT/EP2014062461, 4 pages.
(Continued)

*Primary Examiner* — Pedro Philogene
*Assistant Examiner* — David C Comstock
(74) *Attorney, Agent, or Firm* — Morrison & Foerster LLP

(57) ABSTRACT

An implantation instrument for an expandable intervertebral fusion implant that includes a base piece and a cover piece that are configured to bear on a facing end plate of one of two adjacent vertebrae, the cover piece being adjustable in height with respect to the base piece, and a ratchet mechanism being provided between the base piece and the cover piece to effect a stepped adjustment of height and secure an adopted height again reversal, the implantation instrument being configured for expanding the intervertebral fusion implant and comprising a force measurer that interacts with a displacement measurer to indicate an expansion attained by a particular actuating force.

18 Claims, 8 Drawing Sheets

(51) Int. Cl.
*A61F 2/46* (2006.01)
*A61F 2/30* (2006.01)

(52) U.S. Cl.
CPC ............... *A61F 2002/30377* (2013.01); *A61F 2002/30477* (2013.01); *A61F 2002/30494* (2013.01); *A61F 2002/30522* (2013.01); *A61F 2002/30579* (2013.01); *A61F 2002/4475* (2013.01); *A61F 2002/4666* (2013.01); *A61F 2002/4697* (2013.01)

(58) Field of Classification Search
CPC .. A61F 2002/30494; A61F 2002/30522; A61F 2002/30579; A61F 2002/4475; A61F 2002/4666; A61F 2002/4697
USPC .................. 606/246, 99, 102, 90, 105, 86 A; 623/17.15, 17.16
See application file for complete search history.

(56) References Cited

U.S. PATENT DOCUMENTS

| | | | |
|---|---|---|---|
| 6,176,881 B1 | 1/2001 | Schär et al. | |
| 2007/0123987 A1 | 5/2007 | Bernstein | |
| 2007/0288092 A1 | 12/2007 | Bambakidis | |
| 2009/0138021 A1* | 5/2009 | Colquhoun | A61B 17/025 606/88 |
| 2012/0226356 A1 | 9/2012 | Hirschl | |
| 2013/0131808 A1 | 5/2013 | Suh et al. | |
| 2014/0188225 A1 | 7/2014 | Dmuschewsky | |
| 2014/0214043 A1* | 7/2014 | Lim | A61B 17/025 606/90 |

FOREIGN PATENT DOCUMENTS

| | | |
|---|---|---|
| JP | 2000-210315 | 8/2000 |
| WO | WO-98/46173 | 10/1998 |
| WO | WO-00/25706 | 5/2000 |
| WO | WO-00/35389 | 6/2000 |
| WO | WO-03/032812 | 4/2003 |
| WO | WO-2004/073562 | 9/2004 |
| WO | WO-2014/091030 | 6/2014 |

OTHER PUBLICATIONS

International Preliminary Report on Patentability dated Dec. 15, 2016, directed towards International Application No. PCT/EP2014062461, 7 pages.

* cited by examiner

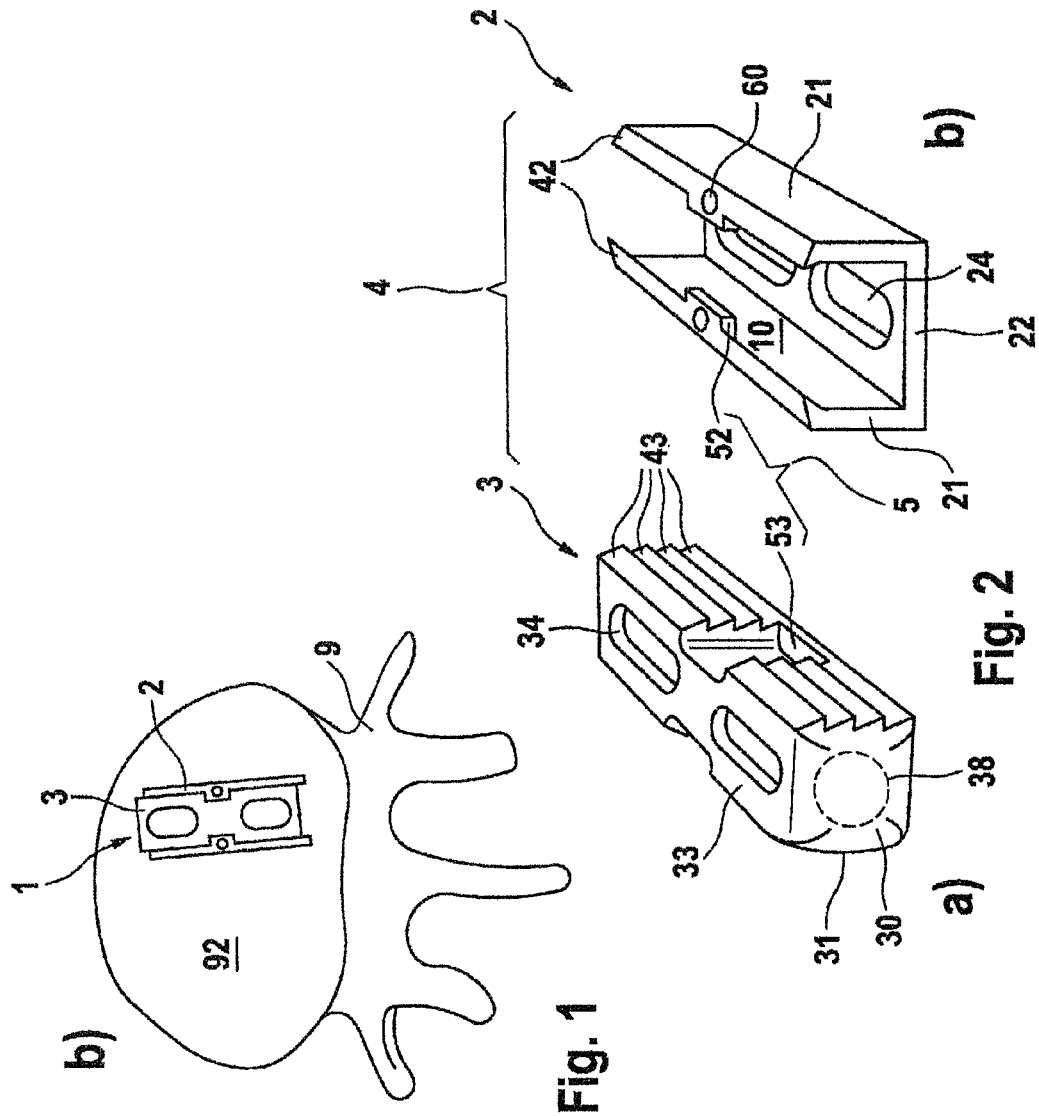
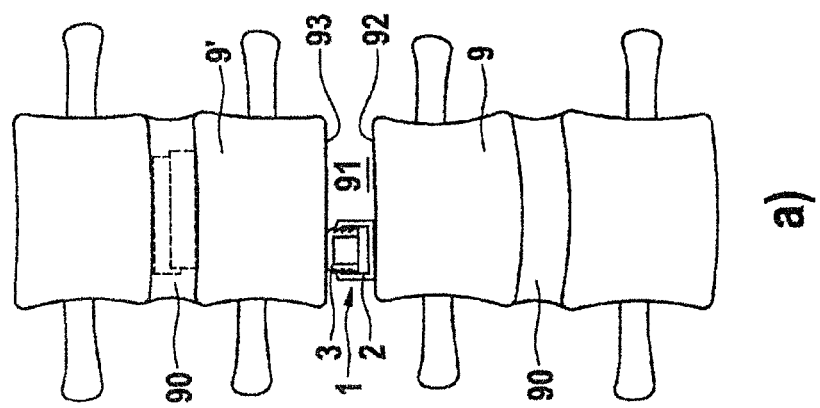

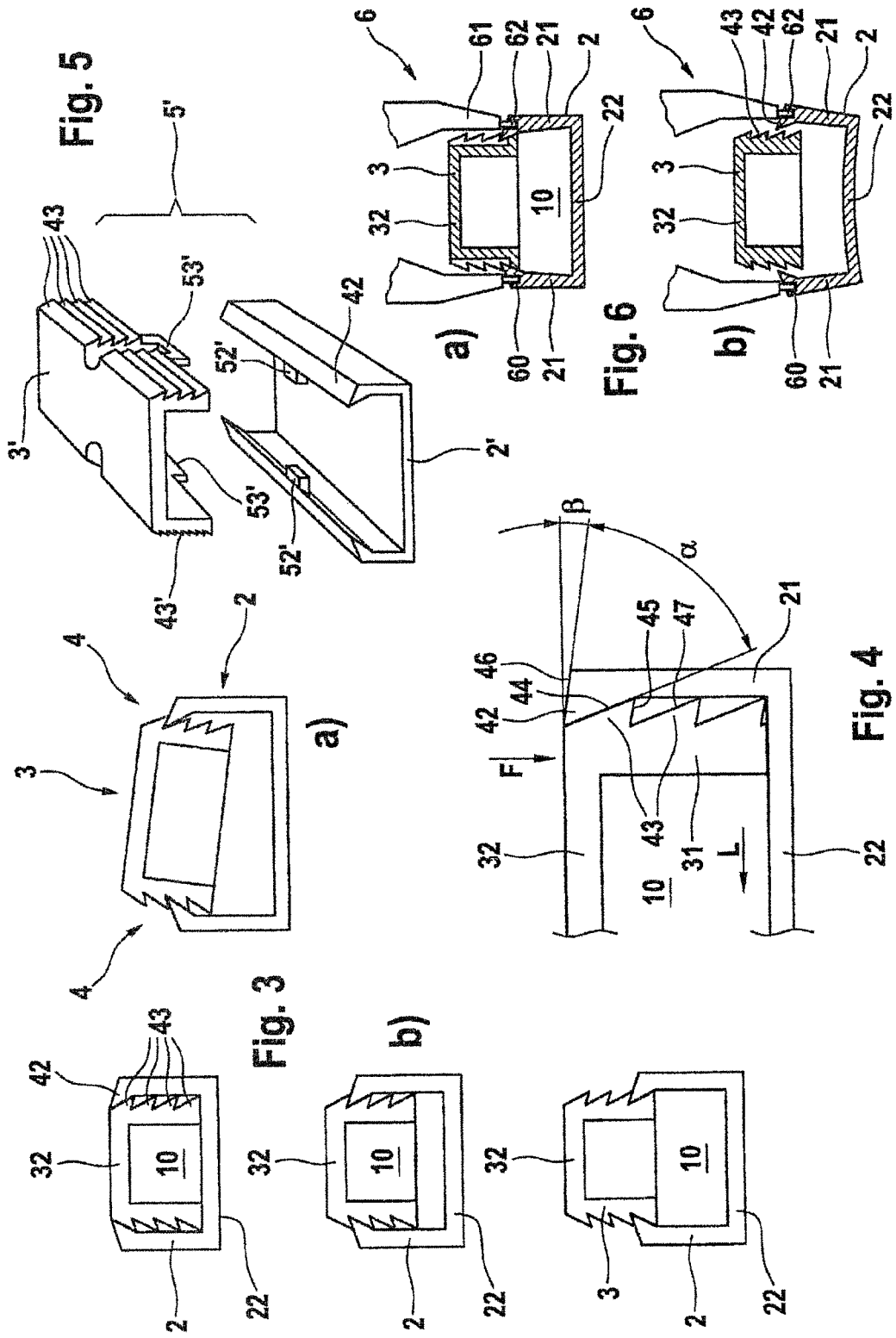

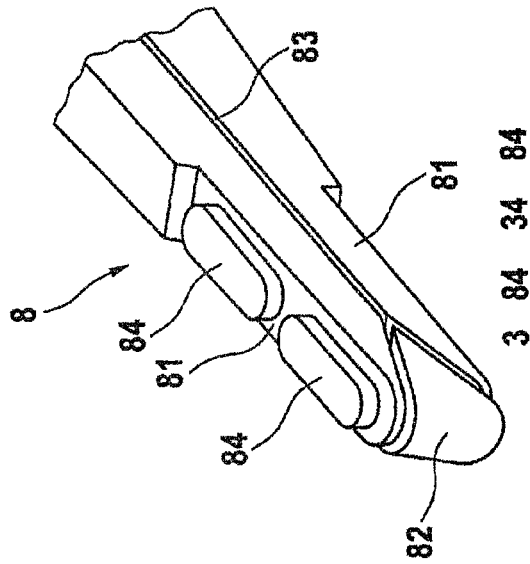
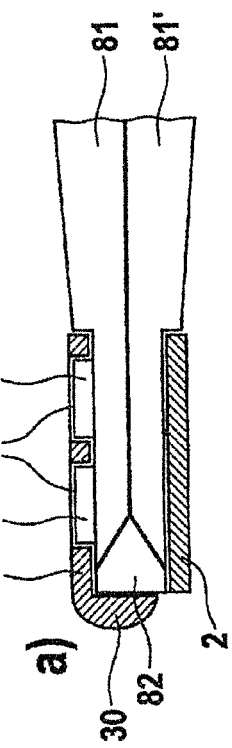
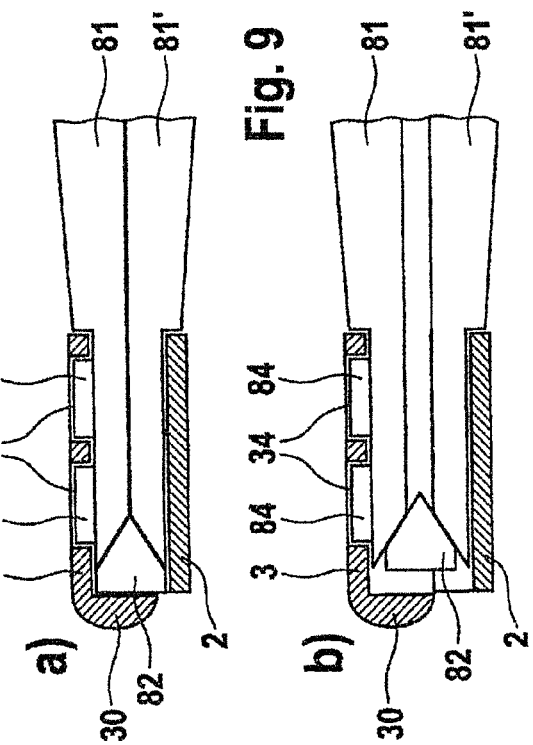
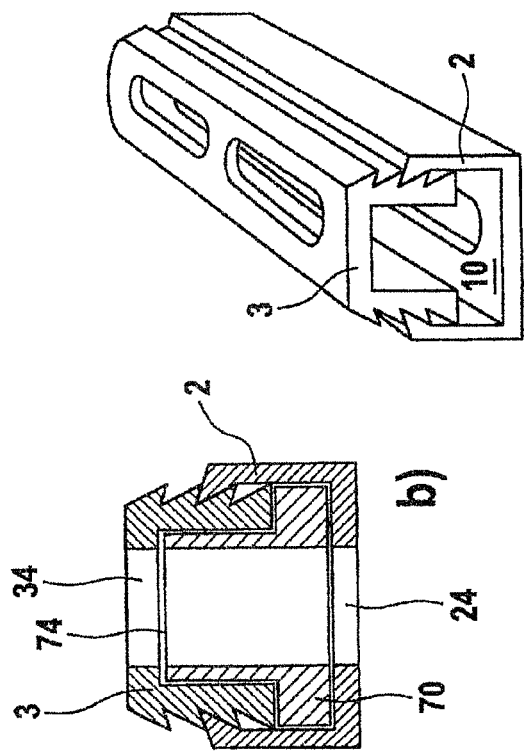
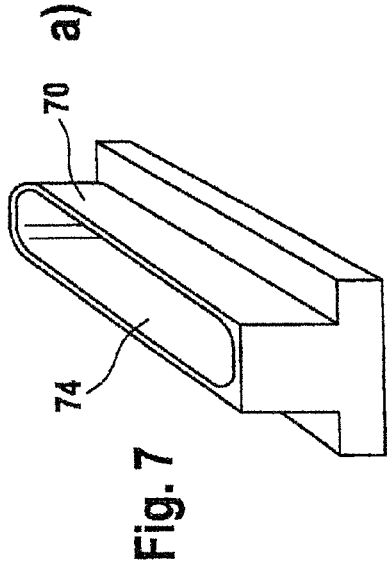

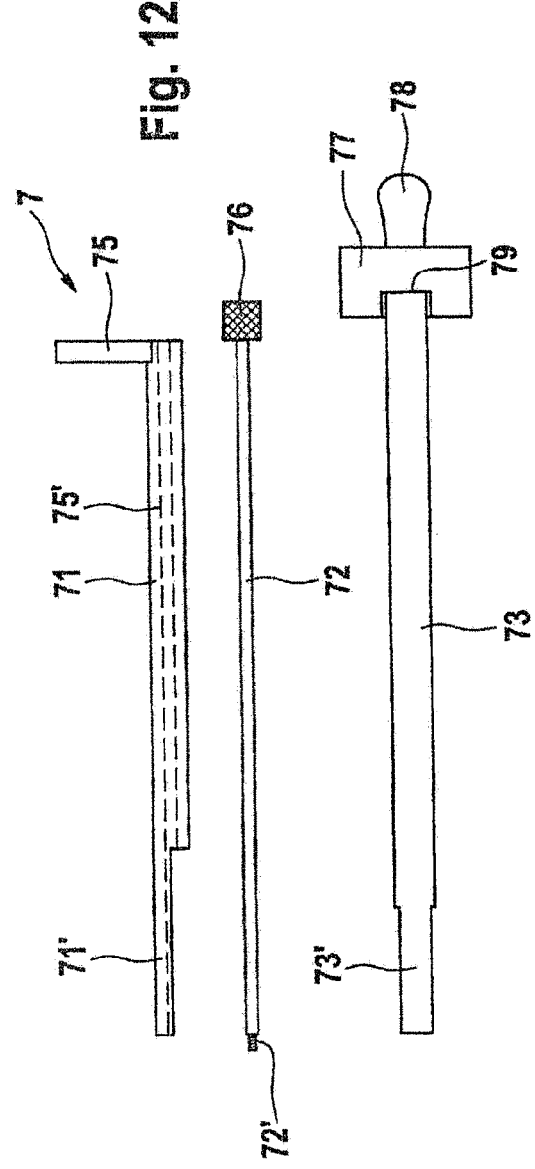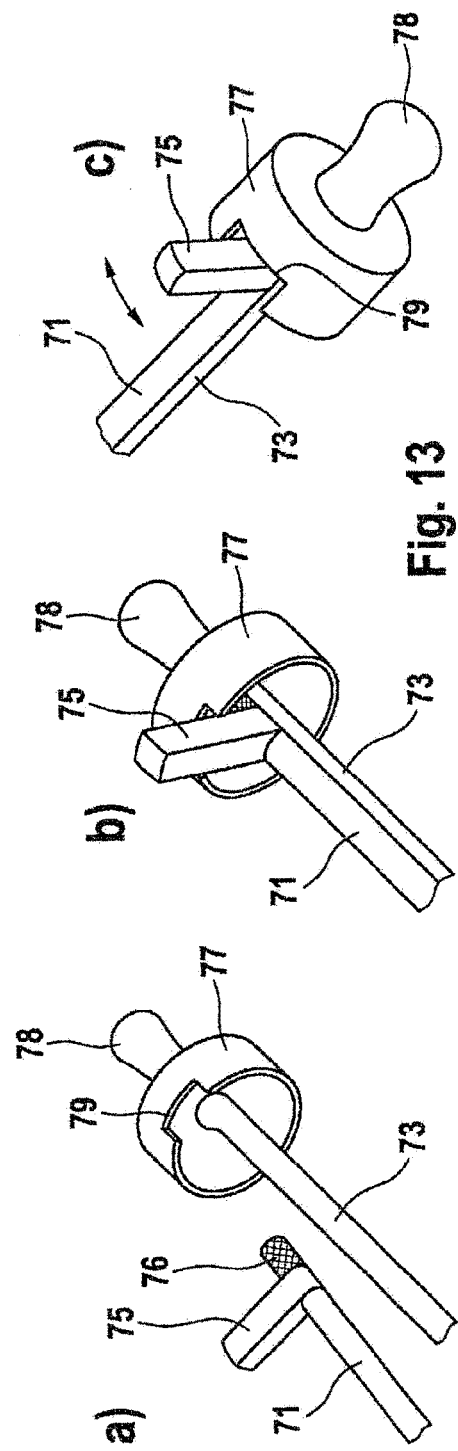

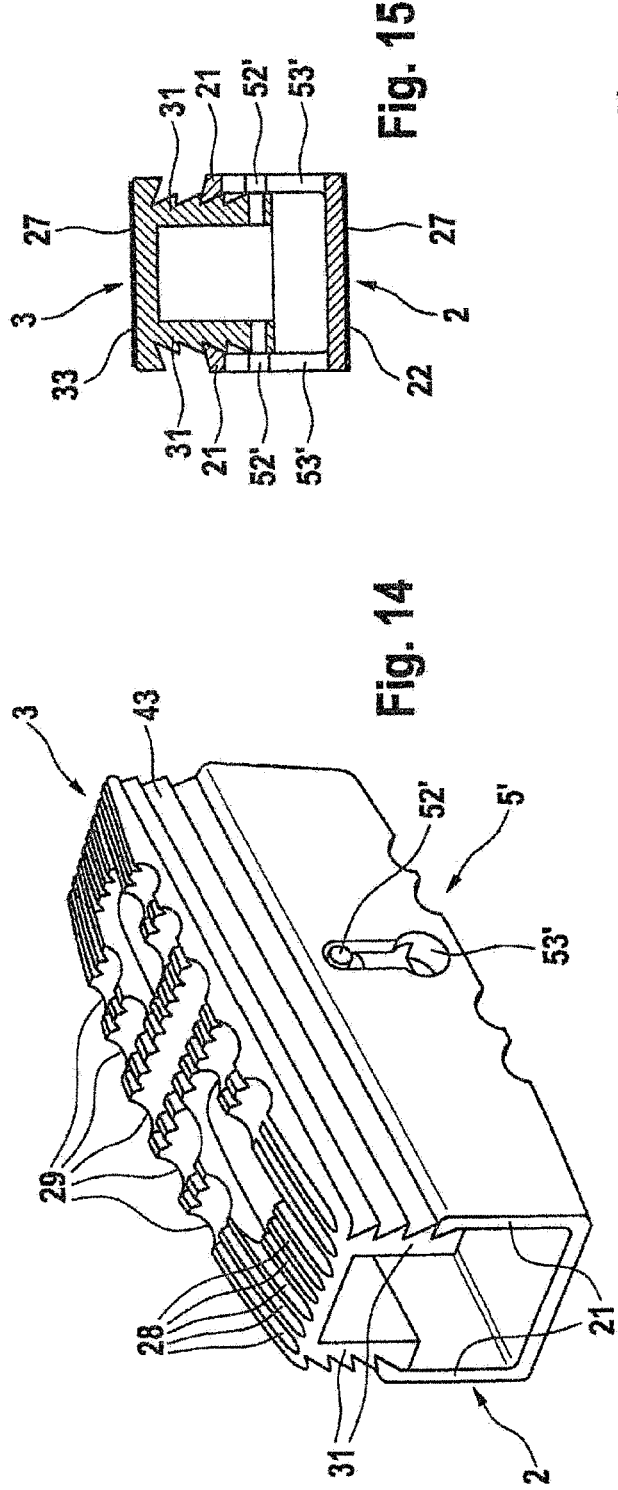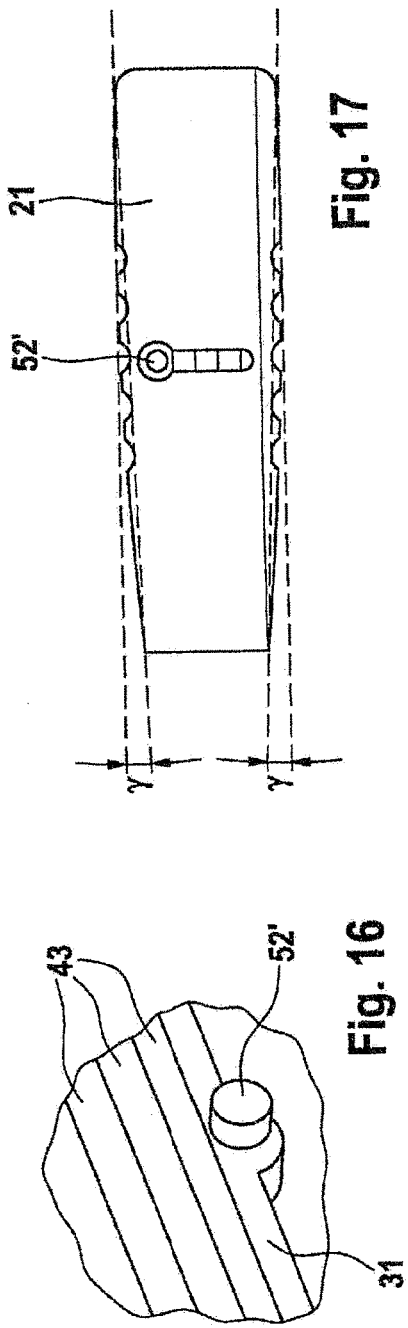

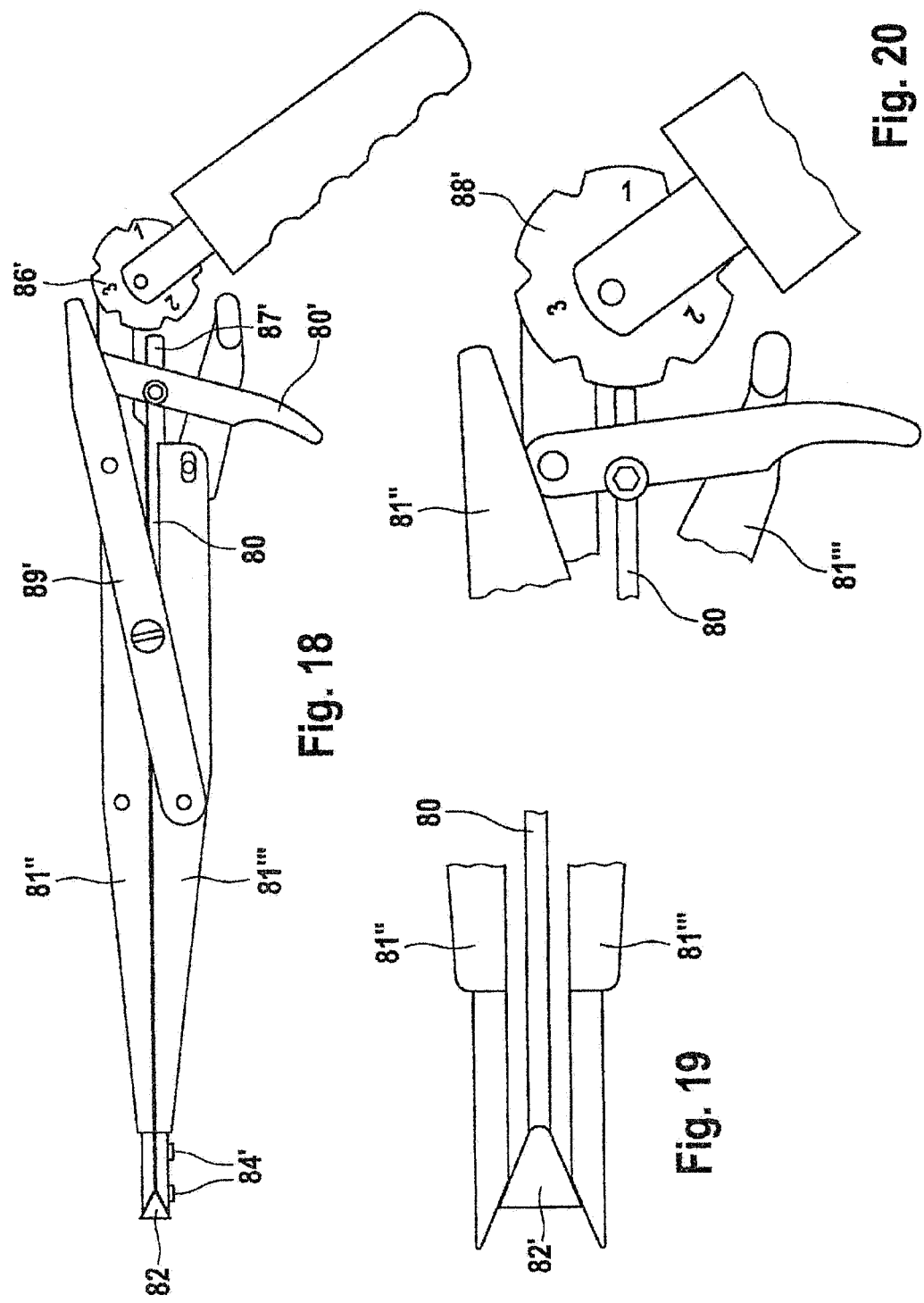

INTERVERTEBRAL CAGE WHICH IS EXPANDABLE IN STEPS AND IMPLANTATION INSTRUMENT THEREFOR

CROSS-REFERENCE TO RELATED APPLICATIONS

This application is a national stage application under 35 USC 371 of International Application No. PCT/EP2014/062461, filed Jun. 13, 2014, the entire contents of which are incorporated herein by reference.

FIELD OF THE INVENTION

The invention relates to an intervertebral cage that is expandable in steps, with a bottom piece and a cover piece for bearing on end plates of an upper and lower adjacent vertebral body, respectively, and to an implantation instrument.

BACKGROUND OF THE INVENTION

The intervertebral disks of the spinal column suffer degeneration as a result of wear or of pathological changes. If conservative treatment by medication and/or physiotherapy is ineffective, surgical treatment is sometimes indicated. In this connection, it is known for a movable or immovable implant to be inserted into the intervertebral space containing the degenerated intervertebral disk. These implants take over the support function of the degenerated intervertebral disk and to this extent restore a stable bearing between the adjacent vertebrae. Immovable implants are also referred to as "cages".

Various surgical techniques are known for implanting the cages. A traditional surgical technique involves a ventral access route, in order thereby to avoid the danger of damaging the spinal cord in the vertebral column. However, this advantage is obtained at the price of a very long access route through the abdominal cavity or thoracic cavity of the patient. Since this can cause complications, an alternative access route has become established, namely from the dorsal direction. Although the latter affords the advantage of a short route, there is the danger of collision with or damage to the spinal cord. To minimize this danger, the operation is usually performed by minimally invasive surgery. Approaches of this kind directly from the dorsal direction or more from the side are known as PLIF (posterior lumbar intervertebral fusion) or TLIF (transforaminal lumbar interbody fusion), in which the intervertebral disk is exposed from the posterior or lateral direction, respectively. Because of the small transverse incisions used in an approach by minimally invasive surgery, the size of the cage is of course greatly restricted.

For treatment using the PLIF or TLIF technique, very small cages are known. They afford the advantage of being able to be implanted by minimally invasive surgery thanks to their small size. However, an inherent disadvantage of their small size is that the support function is limited because of the small dimensions and is sometimes inadequate. Although a larger size of the cages would improve the support function, this is impractical because of the limits of minimally invasive surgery.

SUMMARY OF THE INVENTION

According to some aspects, the invention can address the problem of improving a cage of the type mentioned at the outset in such a way that a better supporting action can be achieved while still using a small access cross section of the kind customary in minimally invasive surgery.

Solutions according to the invention lie in the features of the independent claims. Advantageous developments are the subject matter of the dependent claims.

In an intervertebral fusion implant for fusion of two adjacent vertebrae, comprising a base piece and a cover piece for bearing on end plates of lower and upper adjacent vertebrae, wherein the cover piece is adjustable in height with respect to the base piece, provision is made according to the invention for a ratchet mechanism between base piece and cover piece, which ratchet mechanism effects a stepped adjustment of height and secures an adopted height against reversal. The ratchet mechanism is preferably designed such that the base piece has a bottom wall, for bearing on the lower vertebra, and a vertical wall rising from this bottom wall, and the cover piece has a cover wall, for bearing on the upper vertebra, and a side wall projecting downward from this cover wall, said vertical wall and side wall being parts of the ratchet mechanism. Here, the ratchet mechanism expediently has a plurality of locking lugs on the side wall and a locking spring on the vertical wall, or vice versa.

Aspects of the invention are based on the concept of using a fusion implant that is adjustable in height such that, at the time of implantation, it can be introduced in the compact state through the minimally invasive access route into the intervertebral space and can be expanded there in height. This is done by actuating a height adjustment mechanism, which is designed as a ratchet mechanism. In this way, a defined expansion can be achieved that depends on the number of actuations. This allows the surgeon precise control of the state of expansion, specifically by purely haptic means. The invention is therefore free of limitations of the kind that would arise with purely visual control of the state of expansion (if appropriate by X-ray).

Moreover, the expansion state that has been set can be locked using the ratchet mechanism. The form fit of the ratchet mechanism provides protection against inadvertent return movement, even under very high loading forces. This results in excellent stability, specifically also immediately after the operation, until complete fusion of the two adjacent vertebral bodies is finally achieved by bone growth.

A double ratchet mechanism is advantageously provided, preferably one on each lateral face of the implant. On the one hand, this provides secure support, even under loads that are not exerted centrally. On the other hand, a double ratchet mechanism of this kind makes it possible to give both sides different heights, which results in a defined tilting of the cover piece with respect to the base piece. In this way, an adaptation to curvatures in the spinal column can be made in the respective intervertebral space. For this purpose, provision can also be made that the two ratchet mechanisms are offset in height with respect to each other, preferably by an offset of their respective locking lugs.

Two vertical walls are preferably provided laterally on the bottom wall, and the bottom wall is elastic. This permits a flexible, reversible spreading open of the two vertical walls, such that the expansion movement is made easier. At the same time, by purposeful spreading open of the two side walls, a resetting possibility can be made available for the cover piece. This permits testing of the fusion implant and resetting in the event of overexpansion. In an alternative variant, only the vertical walls are elastic, while the bottom wall is stiff. Bulging of the bottom wall is thereby avoided.

The cover piece is preferably made from a less elastic material than the bottom piece. For example, the cover piece is made from a cobalt-chromium alloy, whereas the base piece is made from a more elastic titanium alloy. It is thus possible to achieve a greater force uptake, in particular at the locking lugs of the ratchet mechanism.

In order to prevent accidental overexpansion, a catch mechanism is preferably provided which limits the adjustment movement of the cover piece. The catch mechanism is expediently formed by a pawl that interacts with a shoulder projection. Harmful overexpansion is thus prevented in a simple and efficient manner. In an alternative embodiment, the catch mechanism is formed by slots in the vertical walls and a by transverse pin which protrudes laterally from the side walls and engages in the slots. The transverse pin is preferably arranged at the bottom on the side walls. In this way, the locking teeth on the side walls are able to run through without interruption, which improves the force transmission.

To permit fine adjustment in the case of double ratchet mechanisms, the locking lugs on one of the two ratchet mechanisms are preferably designed such that they have a spacing which is an integral multiple of the spacing of the locking lugs on the other of the two ratchet mechanisms. For example, the spacing on one ratchet mechanism is twice as great as the spacing on the other one. On the one hand, a rapid adjustment can thus be achieved by the greater spacing. On the other hand, a finer adjustment can be obtained using the ratchet mechanism with the smaller spacing, which is a considerable advantage in practice, in particular as regards adjustment of an angle of tilt between cover piece and base piece.

A suitable size of the spacing of the locking lugs from one another is approximately 1.5 to 3.0 times their elevation (which is defined by the distance between tooth tip and tooth bottom).

The locking lugs are advantageously designed asymmetrically, preferably in a sawtooth shape. This allows a configuration which is such that only a low force is needed for the expansion, by virtue of favorable flank angles, whereas high retention forces are applied against return movement. It has proven suitable if the angle of a supporting flank is in the range of 5 to 35°, preferably approximately 10°. The supporting flank is understood as being the one that bears the load and thus counteracts a return movement. The sawtooth shape is preferably such as to give a tooth angle in the range of 45° to 70°, preferably approximately 60°. In a particularly expedient embodiment, the locking lugs overlap one another in an imbricated manner, wherein the counter-flank is preferably oriented in the same direction as, but flatter than, the supporting flank. This configuration permits a particularly favorable adjustment of the force relationships between the actuating force during the expansion and the retention force with respect to return movement. This can be further increased if the locking spring engages with a form fit in the locking lugs, wherein the shape of the locking lugs is preferably adapted to the locking spring such that a self-securing effect is achieved. This provides maximum securing against undesired return movement, which is ultimately defined only by the load limits of the material with respect to fracture or shear.

To maximize the self-securing effect, the interacting surfaces on locking lug and locking spring are not parallel, but instead oriented at an acute angle to each other. At an acute angle is understood here as meaning that the respective surfaces diverge from each other in the direction toward the bottom of the locking teeth. This configuration has the effect that, under a load, the locking spring draws further between the locking teeth. An undesired escape of the locking spring from the locking teeth is thus safely avoided. The securing effect is thus maximized.

An inner hollow space is preferably formed between cover piece and base piece. This permits introduction of bone substance, such as grafts or chips, in order thereby to promote inward growth of bone substance for stiffening. In order to promote introduction of bone substance, and in particular also inward growth from the direction of the two adjacent vertebrae, at least one aperture is preferably provided on the cover plate and/or bottom wall and is connected to the hollow space.

A blocking element can also be provided, which can be pushed into the hollow space. In this way, after implantation and expansion to the desired height, the cover piece can be fixed in its position. An additional securing effect is thus obtained. A plurality of blocking elements with different heights are preferably provided, such that a blocking element can be pushed in that is of the right fit for the expansion. Preferably, at least one additional aperture is provided on the blocking element and is flush with the aperture on the cover plate and/or bottom wall. Thus, growth of bone substance into the hollow space can be promoted even when the blocking element has been pushed in. Moreover, the cover piece and/or base piece can preferably have openings on their end faces. On the one hand, this further promotes inward growth, and, on the other hand, bone substance can be introduced into the hollow space through this end opening even after implantation.

The cover piece and/or base piece is advantageously rounded at its end faces, in particular at its corners. This makes it easier to push the fusion implant according to the invention into the intervertebral space.

The top face of the cover piece and/or the bottom face of the base piece is preferably structured. This is understood to mean that it has regular elevations and depressions. These are preferably fine grooves extending longitudinally, that is to say in the direction from end face to end face, and/or furrows extending transversely, that is to say from side wall to side wall. The grooves have a spacing of at least 0.2 mm to at most 1 mm, while the furrows have a width of at least 2 mm and preferably not more than 5 mm. The fine grooves act like teeth and hold the intervertebral fusion implant in place. The furrows protect it from migration, particularly under the effect of a force, as often occurs when the patient stoops or bends down. Moreover, they initially secure the intervertebral fusion implant against slipping. Advantageously, the top face and/or bottom face are provided with a coating of titanium plasma spray, which promotes inward growth of bone substance. The titanium plasma spray is preferably finely particulate with a grain size of at most 90 µm, such that it does not even close fine structures such as said grooves. Preferably, the edge areas toward the end faces are smooth or are provided only with the grooves and not with the furrows. This ensures a greater load-bearing capacity for the cortical vertebral margin.

The overall configuration of the intervertebral fusion implant is preferably generally box-shaped. This is favorable from the point of view of production technology and simplifies introduction of the implant in a straight line into the intervertebral space. However, it may also be desirable that the implantation does not take place in a straight line but instead in an arc shape. For this purpose, the intervertebral fusion implant is preferably curved in the shape of an arc of a circle. This simplifies implantation, particularly in the case of an access route obliquely from behind by means of the TLIF (transforaminal lumbar interbody fusion) technique.

The intervertebral fusion implant can also be wedge-shaped, in such a way that one end wall is lower than the other. Wedge angles in the range of approximately 3° to 15° are preferred. This can allow better adaptation to a curvature of the spinal column, in particular to a lordosis.

It may be expedient to return the already expanded intervertebral fusion implant to the compact size in which it is provided for implantation. This can be done after an extracorporeal test of functionality or following an (over) expansion performed for test purposes. In order to be able to reset the intervertebral fusion implant, a release mechanism for the ratchet mechanism is provided. In a simple case, it can be in the form of seats that are arranged at the free end of the vertical wall and/or side wall and are provided for a laterally acting spreading element. This spreads the vertical walls open, such that the locking teeth move out of the area of engagement of the locking spring, and the cover piece can be moved back again relative to the base piece. In a preferred embodiment, seats are designed as holes at the upper end of the vertical wall, preferably in the area of the pawl. This permits a particularly simple resetting option, albeit only in a state outside the intervertebral space.

A particularly suitable spreading element is a forceps-like instrument which has grippers that engage in the seats.

The invention further extends to an implantation instrument designed for insertion and actuation of the intervertebral fusion implant. The implantation instrument is preferably designed such that it has a cross section which at most is as great as that of the intervertebral fusion implant. This ensures that the expansion using the implantation instrument can take place through the same small minimally invasive access route used for the actual insertion of the intervertebral fusion implant. A second separate access route is therefore not needed. This therefore reduces the work involved and also places less strain on the patient.

The implantation instrument can be designed as a drawkey expander with two spreading jaws. The draw key is preferably arranged in the front area on the spreading jaws. By moving the draw key, an expansion of the spreading jaws can be effected, which spreading jaws in turn act from the inside on the cover piece or the base piece and thus expand these.

For the movement of the draw key, a tensioning member is preferably provided, which is routed rearward between the spreading jaws. Here, rearward means being routed outward away from the implant in the direction of the surgeon. This allows the surgeon comfortable actuation from the outside via the minimally invasive access. The routing of the tensioning member between the spreading jaws permits a compact structure. Moreover, this permits good protection of the tensioning member against mechanical impairment. The tensioning member is advantageously designed as an actuation spindle. This permits a precise adjustment and also allows reversible actuation by rotation in the opposite direction.

In a well proven embodiment, the draw key is arranged at the front end of the actuation spindle, and an adjustment wheel is mounted at the rear outer end. This permits a comfortable reversible actuation from the outside.

It may in principle also be sufficient for tactile feedback to give the surgeon an idea of the extent of the height adjustment. However, it may also be advantageous if the implantation instrument has a display mechanism, which indicates the attained height adjustment of the intervertebral fusion implant. For this purpose, the display mechanism has a presentation proportional to the attained height adjustment. This makes it easier for the surgeon to determine the expansion that has already been attained.

Alternatively, an implantation instrument can also be provided as a rotary lever plate. It comprises a guide part and a lever part guided pivotably in the latter, wherein seats for either the base piece or the cover piece are provided on both. It is expediently configured such that the base piece is mounted at a front end of the guide part, while the cover piece is mounted on the lever part so as to rotate therewith. For this purpose, a screw connection is expediently provided at the front end of the lever part and engages in a corresponding mating thread of an opening in the end face of the cover piece.

The lever part preferably has a toggle for actuation at its rear end. It is mounted in the guide part, which for this purpose is designed such that the lever part is mounted movably in the radial direction. This means that, by pivoting the toggle in the radial direction, the lever part correspondingly rotates.

The lever part also preferably has an axial bore through which a fastening spindle is fitted. It serves for the easily releasable fastening of the cover piece on the lever part. It has proven useful to provide, on the guide part, a bell with a recess for the toggle.

Here, the recess is shaped such that, in the radial direction, it has a greater width than corresponds to a thickness of the toggle. The toggle is thus movable in the radial direction in the bell and can thus be moved to and fro. This reciprocating movement transfers to the cover piece firmly screwed on the front end, which cover piece accordingly tilts and thus migrates upward alternately on the two ratchet mechanisms by in each case one further locking tooth. A height adjustment is effected in this way. Moreover, if tilting is desired, a tilt can be adopted by means of an uneven number of actuation procedures.

A further alternative implantation instrument is designed as a parallel expander with cross lever. The cross lever forms a reverse kinematics system, as a result of which the expander spreads open when pressure is applied to the handle. This kinematics system is more expedient in use than simple forceps without a cross lever, where the handle would have to be spread open. Moreover, the parallel expander preferably has an adjustable limit stop device. With this, a maximum expansion can be fixed, which is then not exceeded. This is particularly advantageous in implantation situations where access conditions are difficult, since the surgeon, during the expansion procedure, no longer has to manually control the position attained. A rotary wheel with a plurality of predefined and inscribed positions is expediently provided. With this, the limit stop device is adjusted accordingly. The desired degree of expansion can therefore be easily adjusted.

The spreading jaws are preferably designed differently as regards the retention of base piece and cover piece. Devices for form-fit connection are preferably arranged on only one of the spreading jaws, preferably in the form of projections engaging in openings in the base piece. By means of the different design, a fail-safe coding is obtained in the sense that the intervertebral fusion implant can only be correctly received with one orientation by the implantation instrument. Errors caused by the implant being received the wrong way round are thus ruled out.

In another embodiment, the implantation instrument is provided with a force-measuring device, which interacts with a displacement-measuring device in such a way that it indicates the expansion travel attained with a respective actuating force. A relationship between actuating force and expansion travel is thus established and indicated to the operator. The operator is thus able to check whether the actuating force applied is sufficient to achieve the desired expansion. Moreover, he is thus able to determine what force is needed for a defined desired expansion. The operator is thus provided with a measure of the elasticity or the stiffness of the spinal column with respect to enlargement of the intervertebral space by expansion. He can thus ascertain at an early stage if, at a defined force, there is a threat of expansion being too great, and can thus can avoid injury to nerves and ligaments. He can likewise ascertain how great the actuating force needed for a desired expansion for insertion of the implant and, if appropriate, can take action if there is a threat of the actuating force reaching values that are too high. This therefore effectively counteracts overloading of or injury to the spinal column with its nerves and ligaments.

The instrument is expediently designed likewise as a parallel expander, preferably with a cross lever as a reverse kinematics system. In this way, a pressing (closing) hand movement by the operator can easily be converted into a parallel expansion movement of the spreading jaws.

The actual actuation preferably takes place via a lever which acts on a transmission element expediently designed as a force-measuring device. In this way, the actuating force can be determined directly. Since the transmission element is supported on the rear end (toward the grip) of the tensioning member, it is thus possible to ensure that the force thereby measured is also exactly the force that acts on the tensioning member and thus ultimately on the spreading jaws.

A particularly expedient embodiment of the force-measuring device comprises a spring element and a force scale that indicates a measure for the spring stroke. In this way, a force measurement is carried out in a simple and robust manner and in the style of a traditional spring force sensor. To indicate the displacement, a marking is preferably provided on the tensioning member and is assigned a displacement scale. This therefore shows both the actuating force applied and also the expansion stroke thereby achieved. The operator is thus provided with clear information, concerning force and displacement, that is important both for the expansion and also for determination of the stiffness of the spinal column.

The invention further extends to an arrangement composed of the intervertebral fusion implant and of the instrument.

BRIEF DESCRIPTION OF THE DRAWINGS

The invention is explained in more detail below with reference to the attached drawing and on the basis of advantageous illustrative embodiments. In the drawing:

FIG. 1 shows a view of an illustrative embodiment of an intervertebral fusion implant in the implanted state on vertebral bodies;

FIG. 2 shows perspective views of base piece and cover piece as per the embodiment shown in FIG. 1;

FIG. 3 shows schematic views of the action of a ratchet mechanism;

FIG. 4 shows an enlarged view of teeth of the ratchet mechanism as per FIG. 3;

FIG. 5 shows an example of a catch mechanism in a variant of the illustrative embodiment;

FIG. 6 shows views of a release mechanism in the locked position and the unlocked position;

FIG. 7 shows a perspective view and a cross-sectional view of a securing element in the dismantled state and the assembled state;

FIG. 8 shows a perspective view of a grip head for an implantation instrument;

FIG. 9 shows cross-sectional views of the implantation instrument as per FIG. 8 in the relaxed state and partially expanded state;

FIG. 12 shows a two-part implantation instrument for an intervertebral fusion prosthesis as per a third embodiment;

FIG. 13 shows views of the second implantation instrument in a partially assembled state and a fully assembled state;

FIG. 14 shows a perspective view of a further illustrative embodiment of the intervertebral fusion implant;

FIG. 15 shows a cross-sectional view of FIG. 14;

FIG. 16 shows an enlarged detail of FIG. 14;

FIG. 17 shows a side view of a variant of FIG. 14;

FIG. 18 shows a plan view of a fourth embodiment of the implantation instrument;

FIG. 19 shows an enlarged detail of FIG. 18;

FIG. 20 shows another enlarged detail of FIG. 18;

DETAILED DESCRIPTION OF THE INVENTION

Figure 10:
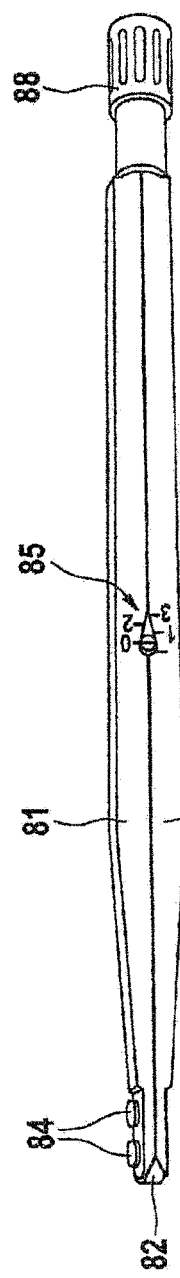
FIG. 10 shows a plan view and cross-sectional details of the implantation instrument.

An intervertebral fusion implant, designated in its entirety by reference number 1, is provided for implantation in an intervertebral space 91 between two immediately adjacent vertebral bodies 9, 9'. In a physiologically intact vertebral column, an intervertebral disk 90 is located in the intervertebral space between the vertebrae. This intervertebral disk 90 may undergo degeneration as a result of disease or wear, with the result that it has to be at least partially resected. In order to achieve sufficient support of the intervertebral space 91, despite the loss of intervertebral disk material, and to thereby prevent collapse of the vertebral column, the intervertebral fusion implant 1 is inserted into the intervertebral space 91. It provides a supporting action and thus facilitates fusion of the two adjacent vertebrae 9, 9' in a natural way through bone growth.

The intervertebral fusion implant 1 comprises a base piece 2, which bears on an upper end plate 92 of the lower adjacent vertebra 9. Moreover, it comprises a cover piece 3, which bears on a lower end plate 93 of the upper adjacent vertebra 9'. In order to ensure a secure bearing of the base piece 2 on the upper end plate 92, on the one hand, and of the cover piece 3 on the lower end plate 93 of the upper vertebra 9', it is necessary to suitably adjust the height of the intervertebral fusion implant 1. It has to be expanded until the base piece 2 and the cover piece 3 bear firmly on the respective end plates 92, 93.

To permit a movement of base piece 2 and cover piece 3 away from each other in the sense of an expansion, a ratchet mechanism 4 is provided. The latter comprises a multiplicity of locking teeth 43 on the cover piece, which interact with a locking spring 42 on the base piece 2.

In order to keep the intervertebral fusion implant 1 according to the invention compact, and thus be able to implant it through an access prepared by minimally invasive surgery, while at the same time allowing it to exert a sufficient supporting action in the intervertebral space 91, the intervertebral fusion implant 1 according to the invention is adjustable in height. For this purpose, it has a base piece 2 and a cover piece 3, which is arranged to be movable in height relative to the base piece 2. The base piece 2 is substantially trough-shaped and comprises a bottom wall 22, which functions as a contact face on the end plate 92 of the lower of the adjacent vertebrae 9, and an upwardly projecting vertical wall 21 on each of the two lateral faces. The base piece 2 therefore has an overall U-shape in cross section. At the upper end of the vertical wall 21, the locking spring 42 is arranged as a part of the ratchet mechanism 4. Moreover, approximately at the middle of an upper end of the vertical wall 21 there is a projection 52, which forms a part of a catch mechanism 5. In the bottom wall 22, there are a plurality of openings 24 via which a hollow space 10, in the interior of the trough-shaped configuration between the side walls 21, is connected to the space underneath the bottom wall 22. This promotes the growth of bone into the intervertebral fusion implant 1.

Moreover, the depicted illustrative embodiment of the intervertebral fusion implant 1 according to the invention comprises a cover piece 3. The latter has a generally box-shaped configuration, with a substantially plane top face 33, which functions as a contact face for the lower end plate 93 of the upper adjacent vertebra 9'. A side wall 31 is arranged projecting downward on each of the lateral faces. On their outward surface, these side walls 31 carry a plurality of locking teeth 43, which form a part of the ratchet mechanism 4 and interact with the locking spring 42 on the base piece 2. In the illustrative embodiment shown, an end wall 30 is provided on an end face. It is optional and can also be omitted. Moreover, a bearing shoulder 53 is also formed approximately at the middle on the side walls 31. Its dimensions are chosen such that it interacts with the projection 52 on the base piece 2. The arrangement of the bearing shoulder 53 is chosen here such that it comes to bear on the projection 52 in the position of maximum extension of the cover piece 3 relative to the base piece 2. A limit stop is thus obtained. The projection 52 and the bearing shoulder 53 thus interact as a catch mechanism 5. A plurality of apertures 34 are formed on the top face 33, in order to allow bone substance to grow into the interior of the cover piece.

For implantation, the cover piece 3 is fitted into the hollow space 10 of the trough-shaped base piece 2. The implant is thus in the state of minimal expansion, as is shown in the uppermost of the three views arranged above one another in FIG. 3a. In this state, the implant is introduced into the intervertebral space 91 until it more or less reaches the position shown in FIG. 1b. In a next step, it can then be expanded until it is set to the height of the intervertebral space 91. This is done by the cover piece 3 being moved upward by means of an implantation instrument 8, wherein the locking spring 42 successively engages with different locking teeth 43 on the lateral faces 31 of the cover piece 3 and thereby secures the attained position of expansion. This expansion procedure is depicted in the three views in FIG. 3a.

The locking teeth 43 are sawtooth-shaped. Each tooth 43 has two flanks 45, 47. Here, the shorter flank 45 is the load-bearing flank, which comes into engagement with the locking spring 42 in such a way as to transmit force. This load-bearing flank 45 is shaped facing downward and is thus oriented in the same direction as the other, non-load-bearing flank 47. This results in a certain degree of imbrication of the locking teeth 43 when viewed from the side. In the illustrative embodiment shown in FIG. 4, the angles α and β are chosen such that the angle α is about 60° and the angle β is 8°. The top face 46 of the locking spring 42 is inclined by said angle β. Thus, together with the downwardly facing orientation of the load-bearing flank 45, this means that a loading force F results in an inwardly directed lateral force L, which draws the locking spring 42 into the teeth 43 and thus secures it against undesired escape from the locking teeth 43. A self-securing effect is thus obtained in the sense that the securing force L increases the greater the loading force F.

In order to prevent a situation in which the cover piece is moved too far up during the expansion and the locking spring 42 thus leaves the area of the locking teeth 43, a catch mechanism 5' as shown in FIG. 5 is alternatively provided. It comprises a projection 52' on each locking spring 42, specifically at the middle thereof. A downwardly facing stirrup 53' is arranged on the cover piece 3, underneath the locking teeth 43, its dimensions being chosen such as to enclose the projection 52'. When the maximum expansion is reached, the stirrup 53' engages under the projection 52' and prevents a further expansion movement.

For the purpose of height adjustment, the expansion movement generally takes place uniformly on both sides of the ratchet mechanism 4, as is also depicted in FIG. 3a. However, it may also be desirable for the adjustment to be non-uniform in order to adopt a defined tilt angle. A desired tilt angle can be adopted in a defined manner depending on whether the adjustment on one side takes place across one or two extra locking teeth 43. For this purpose, the surgeon simply has to count off the number of "clicks", i.e. the number of locking procedures in the ratchet mechanism 4 made by the engagement of the locking spring 42 in the different locking teeth 43. For a finer adjustment of the tilt, more finely stepped teeth 43' can also be provided, twice as many teeth 43' of half the size of the teeth 43. Preferably, only one of the two ratchet mechanisms is provided with the finer teeth, as is shown in FIG. 5. Optionally, the start points of the teeth 43, 43' are mutually offset between the two ratchet mechanisms.

It may be necessary to return the cover piece 3 from its expanded position to a less expanded position or to a position of no expansion at all, as is used for the implantation. For this purpose, a resetting mechanism 6 is expediently provided. This comprises an instrument with forceps-like grippers 61 which, with corresponding gripper tips 62 at their front end, engage in receiving openings 60 formed for this purpose on the top face of the vertical walls 21. By spreading the grippers 61 in a forceps-like movement, the two vertical walls 21 lying opposite each other are moved away from each other, as a result of which the locking spring 42 on the respective vertical wall 21 is no longer in engagement with the locking teeth 43 on the cover piece 3. The ratchet mechanism 4 is thereby released. The cover piece 3 can be freely moved downward and in this way reset. For this purpose, the material of the base piece 2 is preferably chosen such that it is able to deform elastically, in particular the bottom wall 22. This is shown in FIG. 6.

In order to achieve additional securing of the attained height adjustment after successful expansion, a separate blocking element 70 can be provided. It is preferably shaped such that it can be pushed with a good fit into the hollow space 10 between cover piece 3 and base piece 2, which hollow space 10 has been enlarged by the expansion. It will be appreciated that different blocking elements 70 have to be used depending on the expansion status. The blocking element 70 preferably has a central aperture 74, which is flush with the apertures 34 on the cover piece 3 and the apertures 24 on the base piece 2. In this way, the hollow space 10 can be more easily reached and accessible for the inward growth of bone substance. In the inserted state, the blocking element 70 secures the cover piece 3 against a reverse movement back into the base piece 2, as is shown in FIG. 7b.

For the height adjustment by means of expansion, an implantation instrument is provided. It is designed as a draw-key expander 8 with two spreading jaws 81. They are provided at their front end with seats 84, which engage with a form fit in the apertures 34. At the front end, the spreading jaws 81 are indented in a V-shape, and a wedge-shaped draw key 82 is fitted into this indent. The draw key 82 is connected to a tensioning member 80, which extends along the longitudinal axis of the implantation instrument 8, over the entire length of the latter (see FIG. 10). It begins with its front end on the draw key 82 and terminates, at the rear end of the implantation instrument 8, in a handwheel 88, in which it is mounted via a spindle thread 89. When the handwheel 88 is turned, the tensioning member 80 is moved rearward by means of the spindle thread 89, as a result of which the draw key 82 retreats into the V-shaped depression between the two spreading jaws 81. The spreading jaws 81 are thereby driven apart from each other (see FIG. 9, where the top view shows the non-expanded initial state and the lower view shows an expanded state). Depending on the pitch of the spindle thread 89, the surgeon can obtain a desired spreading action by means of a defined number of rotations of the handwheel 88, as a result of which the cover piece 3 is adjusted in height in relation to the base piece 2. For additional control of the attained state of expansion, a display mechanism 85 is provided. It comprises a scale 86 arranged on the spreading jaws 81, and an indicator pin 87 arranged on the tensioning member 80. The indicator pin 87 is drawn rearward together with the tensioning member during the spreading procedure, as a result of which its position relative to the scale 86 changes, and the state of expansion attained can thus be read off.

Figure 11:
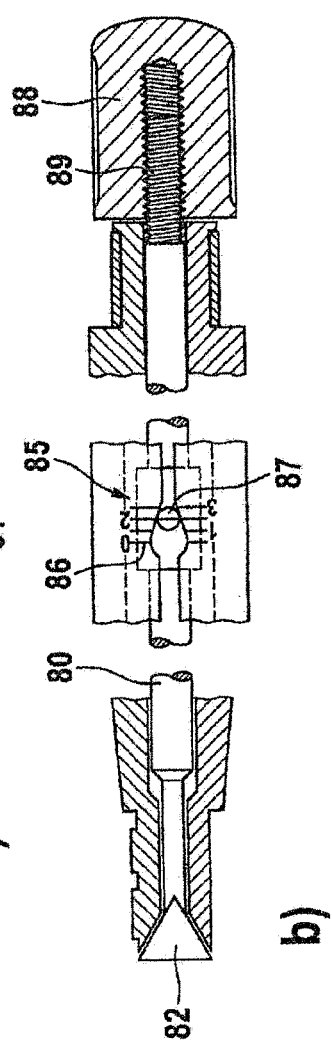
FIG. 11 shows a perspective view of a second embodiment.

A second alternative illustrative embodiment of the intervertebral fusion implant 1' is shown in FIG. 11. Although it is substantially the same as the one in FIG. 1, it differs in that it is not designed rectilinearly in a box shape but is instead substantially curved in the shape of an arc of a circle. As regards structure and function, the above description applies by analogy.

In a further embodiment, which is suitable in particular for a transverse implantation (as is indicated in FIG. 1a by a broken line in the area of the intervertebral disk 90), a further embodiment of the intervertebral implant is provided. In the area of its end face 30, it has an opening in which a part of the implantation instrument can be screwed (see opening indicated by broken lines in FIG. 2a). The implantation instrument 7 provided therefor is shown in FIGS. 12 and 13. The implantation instrument comprises a lever part 71 and a guide part 73. Moreover, a threaded rod 72 is provided, which is to be fitted into an axial bore 75' arranged along the longitudinal axis of the lever part 71. At its rear end, the lever part 71 has a toggle 75 protruding radially to the side. At its front end, the lever part 71 has a gripping jaw 71', which is designed to grip the bottom wall 22 of the base piece 2. At its front end, the guide piece 73 has a second gripping jaw 73', which is correspondingly designed to grip the cover wall 33 of the cover piece 3. At the rear end, the guide piece 73 has a guide bell 77, which is open on one side at the front and, at its rear, closed end, has a central handle 78. On its front edge surrounding the open end of the bell, it has a recess 79. The recess 79 is dimensioned such that, seen in the radial direction, it has a greater width than the toggle 75 of the lever piece 71.

For assembly, the threaded rod 72 is pushed through the axial bore 75' of the lever piece 71 and, with a thread 72' at its front end, is fastened in a screw thread of the opening 38 on the end face 30 of the cover piece 3. It is screwed tightly using a knurled head 76 at the rear end of the threaded rod 72. The lever part 71, with the cover piece 3 fastened thereon, is then mounted on the guide piece 73, specifically in such a way that its toggle 75 engages in the recess 79. The base piece 2 is fitted onto the front end of the actuation piece 73. In this way, the implant is fitted onto the instrument 7 in its assembly position, i.e. non-expanded.

The expansion takes place by means of the cover piece 3 being successively tilted relative to the base piece 2, such that the locking spring 42 always jumps one locking tooth 43 further on one side. This alternate tilting takes place by means of the toggle 75 being pivoted to and fro in the recess 79 from one radial end position to the other radial end position, as shown in FIG. 13c by the double arrow. In this way, the cover piece 3 is successively tilted and thus at the same time expanded. The above description applies accordingly for the further description.

A further alternative embodiment of the intervertebral fusion implant is shown in FIGS. 14 to 17. It is based on the embodiment shown in FIG. 2, and similar components are provided with the same reference numbers and to this extent require no explanation. This embodiment has an alternative catch mechanism 5'. It comprises a transverse pin 52' which is arranged at the bottom of and protrudes from the side walls 31 (see also the detail in FIG. 16). The transverse pin 52' engages in a slot-like aperture 53' formed in the vertical walls 21. By virtue of their extended form in the vertical direction, they permit a height adjustment of the cover piece 2, specifically until the transverse pin 52' finally abuts the upper end of the slot-like aperture 53'. A further movement is thereby prevented. The arrangement of the transverse pin 52' at the bottom on the side walls 31 has the advantage that the toothing 43 on the side walls can run through without interruption. It is therefore stiffer and stronger than the interrupted embodiment shown in FIG. 5.

The embodiment shown in FIG. 14 is moreover provided with a structuring. On its top face 33, and also on its bottom face 22, it has furrows 29 extending in the transverse direction from one side to the other. These are approximately 2 mm wide and serve to provide better anchoring of the intervertebral fusion implant on the end plates 92, 93 of the vertebra 9. The edge area of the top face 33 and of the bottom face 22, later coming to lie in the anterior or posterior area, remains free of the furrows 29, so as not to impair the load-bearing capacity in these areas. A large number of fine grooves 28 are formed in the longitudinal direction and extend from one end face to the other. They have a spacing of approximately 1 mm and likewise serve to provide better anchoring. Moreover, the top face 33 and also the bottom face 22 are provided with a coating of titanium spray 27. It is finely particulate and therefore does not block the grooves 28. This coating promotes the attachment and incorporation of bone substance. It will be noted that the structuring or the coating is not limited just to this embodiment and can equally well be provided in the other embodiments too.

As can be seen from FIG. 17, the intervertebral fusion implant can have a wedge shape with a wedge angle γ. It is therefore better suited for implantation between vertebrae that are arranged in a more strongly curved portion of the spinal column. It will be noted that the wedge shape is not limited just to this embodiment and instead can equally well be provided in the other embodiments too.

A further embodiment of an implantation instrument 8' is shown in FIGS. 18 to 20. In terms of its front area designed to receive the intervertebral fusion implant, is is substantially identical to the instrument shown in FIG. 10. Similar components have the same reference numbers and to this extent require no explanation. The instrument 8' is designed as a parallel expander. It is actuated like forceps, the spreading jaws 81", 81''' being moved rectilinearly away from each other. A particular aspect is that the instrument 8' has a cross lever 89', with which a reverse kinematics system is formed. It functions in the sense that, when the instrument 9' is pressed together in the rear grip area, the spreading jaws 81", 81''' in the front area move away from each other. This greatly simplifies handling. Otherwise, a mechanism with a draw key 82 is provided for the expansion, as also in the instrument shown in FIGS. 9 and 10.

Moreover, the implantation instrument 8' has a limit stop mechanism 87'. The latter limits the adjustment path of the draw key 82' and, consequently, the expansion stroke. For this purpose, a rotary wheel 88' is provided at the rear end of the instrument 8' and can be adjusted to predefined positions. Depending on the position, it forms a limit stop 87' that protrudes to a greater or lesser extent and that is provided for the tensioning member 80, which is actuated via a trigger lever 80'. To obtain expansion of the implant after it has been inserted, the surgeon only needs to actuate the trigger lever 80', specifically until the rear end of the tensioning member 80 bears with its rear end on the limit stop 87 that is adjustable via the rotary wheel 88'. The implant is thus expanded in the desired manner. Markings 86' arranged on the rotary wheel indicate the respective adjustable expansion positions. By adjusting the handwheel 88' to the desired expansion position, it is automatically ensured that the implantation instrument 8' stops when this position is reached. The danger of overexpansion, with the resulting risks to the patient, is thus eliminated.

Figure 21:
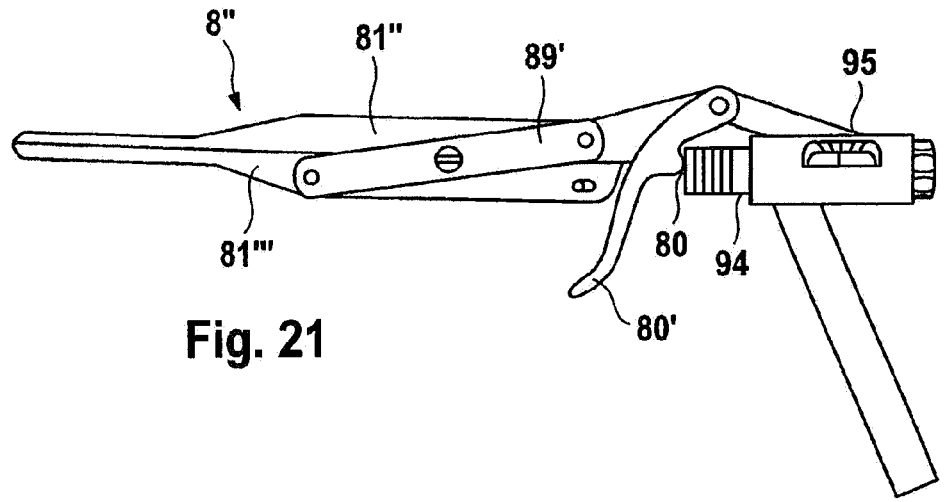
FIG. 21 shows a plan view of a fifth embodiment of the implantation instrument.
Figure 22:
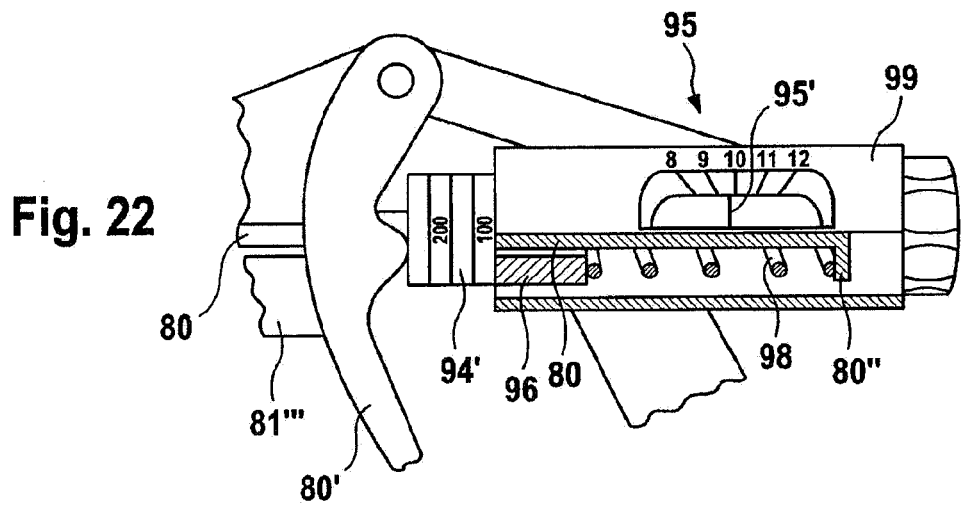
FIG. 22 shows a detail of FIG. 21 in partial section.
Figure 23:
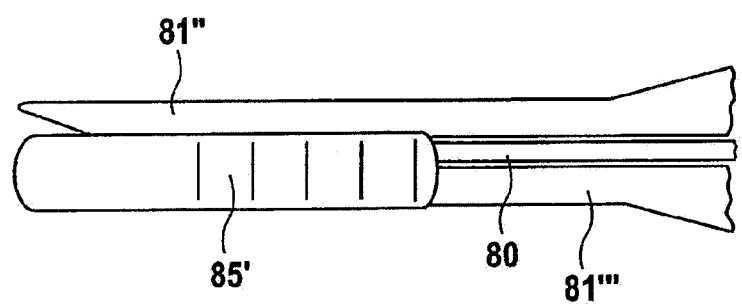
FIG. 23 shows a further detail of FIG. 21.

A variant of the above-described implantation instrument is shown in FIGS. 21 to 23. Components similar to those of the instrument according to FIG. 18 have the same reference signs and to this extent require no explanation. The instrument 8" has a housing 99 on which a grip and a bracket for mounting the trigger lever 80' are arranged. Moreover, a force-measuring device 94 and a displacement-measuring device are provided. The force-measuring device 94 comprises a sleeve 96 and a barrel spring 98. The barrel spring 98 lies with one end on the rear edge 96' of the sleeve 96 and is supported with its other end on a disk 80" which is arranged on the rearward end of the tensioning member 80. Arranged on the sleeve is a scale 94' which, with the front end of the housing 99 as reference, indicates the force applied via the trigger lever 80'. Moreover, a depth scale 85' is provided on one of the spreading jaws 81" in order to define the depth of insertion of the spreading jaws.

For the displacement-measuring device 95, a displacement scale 97 is formed on a viewing hole 99' of the housing 99. It cooperates with a marking 95' on the circumference of the tensioning member 80 and thus allows the displacement path to be read off directly. The displacement scale 97 is calibrated such that it does not indicate the stroke of the tensioning member 80 but instead the expansion travel of the spreading jaws 81", 81'''.

This therefore not only effectively eliminates the danger of overexpansion but also the danger of introducing excessive force, with the resulting risks to the patient.

The invention claimed is:

1. An implantation instrument for an expandable intervertebral fusion implant that includes a base piece and a cover piece that are configured to bear on a facing end plate of one of two adjacent vertebrae, the cover piece being adjustable in height with respect to the base piece, and a ratchet mechanism being provided between the base piece and the cover piece to effect a stepped adjustment of height and secure an adopted height against reversal, the implantation instrument being configured for expanding the intervertebral fusion implant and comprising:
   a tensioning member extending along a longitudinal axis of the implantation instrument and configured for actuating spreading jaws at a front end of the implantation instrument for expanding the intervertebral fusion implant; and
   a force measurer that is configured to directly indicate an actuating force and interacts with a displacement measurer to indicate an expansion attained by the actuating force.

2. The implantation instrument of claim 1, wherein the implantation instrument is a parallel expander.

3. The implantation instrument of claim 2, wherein the implantation instrument comprises a cross lever for forming a reverse kinematics system.

4. The implantation instrument of claim 1, comprising an actuation lever that acts on a transmission element supported on a rear end of the tensioning member.

5. The implantation instrument of claim 4, wherein the force measurer comprises a spring and a force indicator.

6. The implantation instrument of claim 5, wherein the spring is supported on the rear end of the tensioning member, and the force measurer further comprises a sleeve configured to act on the spring.

7. The implantation instrument of claim 4, wherein the transmission element comprises the force measurer.

8. The implantation instrument of claim 4, comprising a force scale arranged on the transmission element.

9. The implantation instrument of claim 4, comprising a displacement scale arranged on the tensioning member.

10. An arrangement comprising:
    an intervertebral fusion implant comprising:
      a base piece and a cover piece that are configured to bear on a facing end plate of one of two adjacent vertebrae, the cover piece being adjustable in height with respect to the base piece, and a ratchet mechanism being provided between the base piece and the cover piece to effect a stepped adjustment of height and secure an adopted height again reversal; and
    an implantation instrument configured for expanding the intervertebral fusion implant and comprising:
      a tensioning member extending along a longitudinal axis of the implantation instrument, and
      a force measurer that is configured to directly indicate an actuating force applied to the implant and interacts with a displacement measurer to indicate an expansion attained by the actuating force.

11. The arrangement of claim 10, wherein the implantation instrument is a parallel expander.

12. The arrangement of claim 11, wherein the implantation instrument comprises a cross lever for forming a reverse kinematics system.

13. The arrangement of claim 10, wherein the implantation instrument comprises an actuation lever that acts on a transmission element supported on a rear end of the tensioning member.

14. The arrangement of claim 13, wherein the transmission element comprises the force measurer.

15. The arrangement of claim 13, wherein the force measurer comprises a spring and a force indicator.

16. The arrangement of claim 15, wherein the spring is supported on the rear end of the tensioning member, and the force measurer further comprises a sleeve configured to act on the spring.

17. The arrangement of claim 13, comprising a force scale arranged on the transmission element.

18. The arrangement of claim 13, comprising a displacement scale arranged on the tensioning member.

\* \* \* \* \*